United States Patent
Aistrup et al.

(10) Patent No.: US 9,549,885 B2
(45) Date of Patent: Jan. 24, 2017

(54) SCALP CARE COMPOSITION

(71) Applicant: The Procter & Gamble Company, Cincinnati, OH (US)

(72) Inventors: Elizabeth Rebecca Aistrup, Cincinnati, OH (US); James Robert Schwartz, West Chester, OH (US); Kenneth LaMont Martin, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/695,172

(22) Filed: Apr. 24, 2015

(65) Prior Publication Data

US 2015/0306006 A1 Oct. 29, 2015

Related U.S. Application Data

(60) Provisional application No. 61/983,749, filed on Apr. 24, 2014.

(51) Int. Cl.
| | | |
|---|---|---|
| *A61K 8/34* | (2006.01) | |
| *A61K 8/49* | (2006.01) | |
| *A61K 8/73* | (2006.01) | |
| *A61K 8/81* | (2006.01) | |
| *A61K 8/86* | (2006.01) | |
| *A61K 8/89* | (2006.01) | |
| *A61Q 5/00* | (2006.01) | |

(52) U.S. Cl.
CPC ............ *A61K 8/4946* (2013.01); *A61K 8/34* (2013.01); *A61K 8/345* (2013.01); *A61K 8/731* (2013.01); *A61K 8/8147* (2013.01); *A61K 8/8152* (2013.01); *A61K 8/8158* (2013.01); *A61K 8/86* (2013.01); *A61K 8/89* (2013.01); *A61Q 5/006* (2013.01); *A61K 2800/49* (2013.01)

(58) Field of Classification Search
USPC .................... 514/63, 79, 396, 399
See application file for complete search history.

(56) References Cited

U.S. PATENT DOCUMENTS

| | | | |
|---|---|---|---|
| 4,329,334 A | 5/1982 | Su et al. | |
| 4,867,971 A | 9/1989 | Ryan et al. | |
| 6,284,234 B1 | 9/2001 | Niemiec et al. | |
| 6,908,912 B2 | 6/2005 | Rioux et al. | |
| 7,001,594 B1 | 2/2006 | Peffly et al. | |
| 7,026,308 B1 | 4/2006 | Gavin et al. | |
| 7,455,851 B1 | 11/2008 | Nelson et al. | |
| 7,674,785 B2 | 3/2010 | Gavin et al. | |
| 8,206,732 B2 | 6/2012 | Nelson et al. | |
| 8,313,782 B2 | 11/2012 | Guthery | |
| D681,876 S | 5/2013 | Murdock et al. | |
| D690,876 S | 10/2013 | Murdock et al. | |
| 8,679,552 B2 | 3/2014 | Guthery | |
| 8,796,252 B2 | 8/2014 | Rioux et al. | |
| 8,858,968 B2 | 10/2014 | Potin | |
| 2003/0008855 A1 | 1/2003 | Simon et al. | |
| 2003/0157088 A1 | 8/2003 | Elliott et al. | |
| 2003/0180242 A1* | 9/2003 | Eccard .................. | A61K 8/0208 424/70.11 |
| 2009/0264449 A1* | 10/2009 | Iwata ....................... | A61K 8/34 514/263.3 |
| 2011/0268684 A1 | 11/2011 | Battermann et al. | |
| 2012/0103151 A1 | 5/2012 | Jones et al. | |
| 2012/0134948 A1 | 5/2012 | Springer et al. | |
| 2012/0251627 A1 | 10/2012 | Nelson et al. | |
| 2013/0115315 A1 | 5/2013 | Derkx | |
| 2013/0284195 A1 | 10/2013 | Murdock et al. | |
| 2014/0349902 A1 | 11/2014 | Allef et al. | |
| 2015/0065476 A1 | 3/2015 | Aistrup et al. | |
| 2015/0306006 A1 | 10/2015 | Aistrup et al. | |

FOREIGN PATENT DOCUMENTS

| | | | |
|---|---|---|---|
| EP | 0639368 A1 | 2/1995 | |
| EP | 0914816 A1 | 5/1999 | |
| FR | 2976801 B1 | 7/2013 | |
| JP | 2005-206538 | 8/2005 | |
| WO | 2007/010478 A2 | 1/2007 | |
| WO | 2010/018418 A1 | 2/2010 | |
| WO | 2013/050241 A1 | 4/2013 | |
| WO | WO2013050241 A1 * | 4/2013 | ............... A61K 8/49 |

OTHER PUBLICATIONS

PCT International Search Report and Written Opinion for PCT/US2015/027410, dated Jul. 15, 2015.
PCT International Search Report and Written Opinion for PCT/US2014/054270, dated Nov. 20, 2014.
"Soothing Serum", Mintel GNPD, Nioxin Research Laboratories, Feb. 2009.
"2-in-1 anti-dandruff & styling gel", Mintel GNPD, Schwarzkopf & DEP, Nov. 2004.
"Gel", Mintel GNPD, Davines, Apr. 2012.

* cited by examiner

*Primary Examiner* — Pancham Bakshi
(74) *Attorney, Agent, or Firm* — Linda M. Sivik

(57) ABSTRACT

A scalp care composition directed to a scalp care composition comprising from about 0.05% to about 5% of an anti-dandruff active, from about 0.1% to about 25% of one or more organic solvents, from about 1% to about 99% of a volatile carrier wherein the anti-dandruff active is soluble in the scalp care composition.

18 Claims, 1 Drawing Sheet

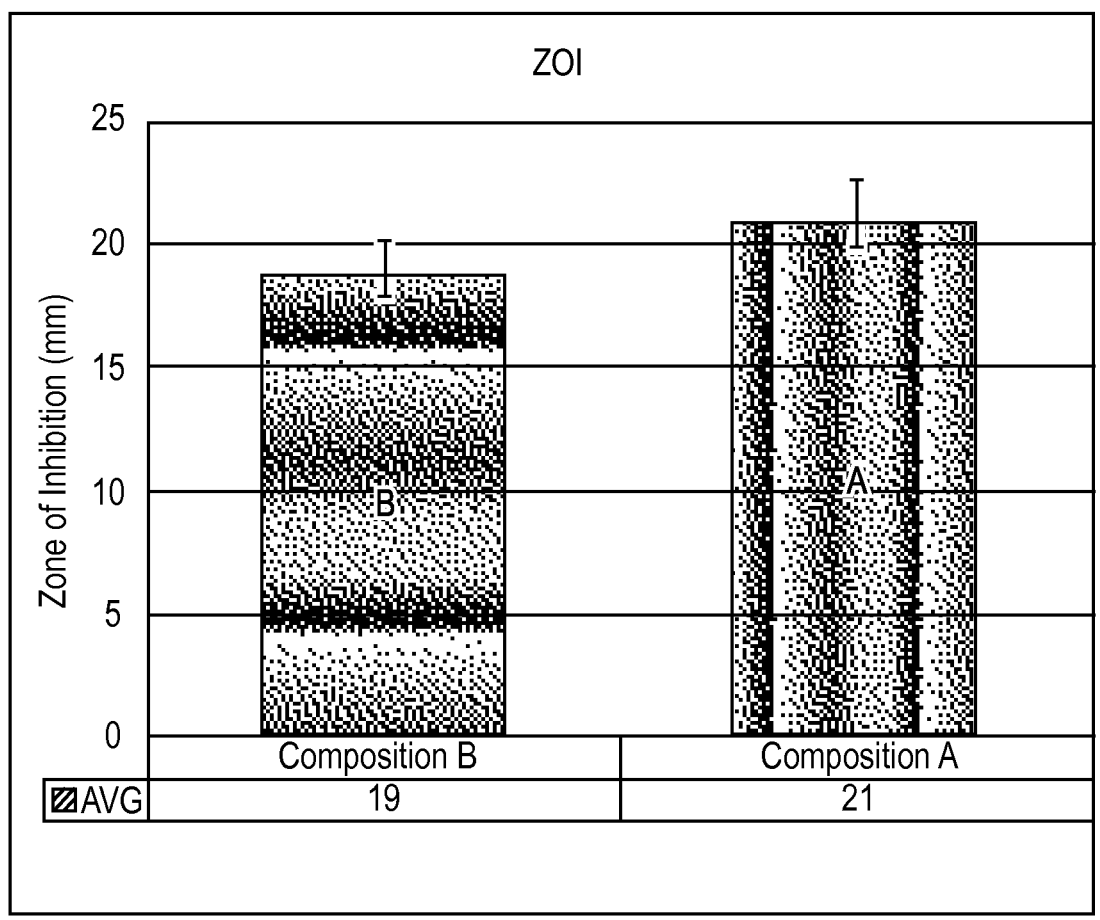

SCALP CARE COMPOSITION

FIELD OF THE INVENTION

The present invention relates to scalp care compositions comprising one or more soluble actives useful for treating dandruff.

BACKGROUND OF THE INVENTION

Hair and scalp leave on treatment compositions comprising various combinations of hair and scalp actives, are known in the art and are commercially available. Anti-dandruff hair rinse off products are also commercially available. Anti-dandruff shampoos, conditioners, and other rinse off treatments typically incorporate an anti-dandruff active. One type of anti-dandruff agents are particulate, crystalline anti-dandruff agents, such as sulfur, selenium disulfide and transition metal salts of pyridinethione. Soluble anti-dandruff agents, such as climbazole, are also available.

Nevertheless, some consumers desire an anti-dandruff leave on treatment which provides a level of anti-dandruff efficacy that can replace other anti-dandruff rinse off products or be in addition to rinse off anti-dandruff products or provide leave on benefits to hair and scalp that are difficult to achieve with a rinse off product. Consequently, a need exists for a treatment product that combines core anti-dandruff efficacy with additional scalp health and hair benefits that the consumer can notice and feel, i.e. effective, and is delightful to use.

It has now been surprisingly discovered that the incorporation of certain formulation solvents can increase the anti-fungal potency of a given composition. These, and other objects, will become readily apparent from the detailed description below.

SUMMARY OF THE INVENTION

In an embodiment of the present invention, it is directed to a scalp care composition comprising from about 0.05% to about 5% of an anti-dandruff active, from about 0.1% to about 25% of one or more organic solvents, from about 1% to about 99% of a volatile carrier wherein the anti-dandruff active is soluble in the scalp care composition. In an embodiment of the present invention, the scalp care composition provides increased anti-fungal potency of the scalp benefit agent.

These and other features, aspects, and advantages of the present invention will become evident to those skilled in the art from a reading of the present disclosure.

BRIEF DESCRIPTION OF THE DRAWINGS

FIG. 1 is a graph depicting zone of inhibition data for a Composition A of the present invention and a comparative Composition B.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Leave-on," in reference to compositions, means compositions intended to be applied to and allowed to remain on the keratinous tissue. These leave-on compositions are to be distinguished from compositions, which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or blockwise—both possibilities are suitable for the present invention. Except if stated otherwise, the term "polymer" used herein includes any type of polymer including homopolymers and copolymers.

There is a need for effective treatments of dandruff. Leave-on scalp treatments have the potential to offer certain advantages over rinse-off products such as shampoos: more efficient delivery of the anti-dandruff active to the scalp surface. Soluble anti-dandruff actives are often used to effectively achieve anti-fungal benefits on the scalp. This property places certain requirements on the development of effective anti-dandruff leave-on treatments. These treatments should contain appropriate solvent combinations such that the active is soluble to a degree that leads to increased efficacy. While not being bound by theory, this increased efficacy is believed to be the result of increased active solubility due to the incorporation of appropriate solvents.

The present invention demonstrates the efficacious solvent composition that has been discovered for an anti-dandruff treatment to effectively deliver soluble anti-dandruff actives to the scalp via direct application. Such compositions may be designed so that the solvent is able to solvate the active and maintain stable and appropriate solubility over time.

In contrast, compositions without the appropriate solvent and/or the sufficient solvent concentration is likely to have an active solubility that leads to decreased anti-fungal activity. Additionally such compositions may result in poor solute stability over time or at temperatures below ambient. Such poor stability would lead to a product that does not deliver sufficient active at each application as it may have crystallized or separated.

I. Scalp Care Compositions

Solvents

According to an embodiment of the invention, the scalp care composition may include one or more solvents. In an embodiment, the scalp care composition may include one or more organic solvents. In a further embodiment of the invention, a solvent may include one or more of the following:

Hydrocarbons, branched or linear saturated or unsaturated (including aromatic) with total carbon atoms less than 15;
Halogenated hydrocarbons, branched or linear saturated or unsaturated (including aromatic) with total carbon atoms less than 15;
Alcohols, diols or polyols with total carbon atoms less than 8;
Thiols or polythiols with total carbon atoms less than 8;
Carboxylic acids with total carbon atoms less than 7;
Carboxylic acid esters or carboxylic acid amides with total carbon atoms less than 8;
Ketones or aldehydes with total carbon atoms less than 8;
Ethers or polyethers with total carbon atoms less than 10;
Amines or polyamines with total carbon atoms less than 8;
Siloxane solvents; and
Materials that contain a combination of the functional groups listed above.

In an embodiment of the present invention, a solvent may be a polyol, an alcohol having an aromatic functional group and combinations. In a further embodiment, a solvent may be butylene glycol, benzyl alcohol and combinations.

In an embodiment of the present invention, a solvent may be present in a range of about 0.1% to about 25%. In a further embodiment, a solvent may be present in a range of about 0.5% to about 20%. In yet a further embodiment, a solvent may be present in a range of about 1.0% to about 15%.

In an embodiment of the present invention, the solvent is volatile. In a further embodiment of the present invention, a solvent may have a boiling point of below or equal to 250° C. In a further embodiment, a solvent may have a boiling point of below or equal to 200° C.

In an embodiment of the present invention, the composition may be anhydrous.

Non-limiting examples of solvents may include dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, benzyl alcohol, 1,3-butanediol, 1,3-propanediol, 2,2'-thiodiethanol, and 1,6-hexanediol, or combinations thereof.

According to yet another embodiment, the hair care composition may further include one or more additional hair growth stimulating agents, such as those disclosed in U.S. Patent Application Publication No. 2010/0120871. Accordingly, non-limiting examples of additional hair growth stimulating agents include indole compounds, xanthine compounds, vitamin $B_3$ compounds, panthenol compounds, and derivatives thereof.

Indole Compounds

The scalp care compositions can further include an indole compound. As used herein, "indole compound" means one or more indoles, derivatives thereof, mixtures thereof, or salts thereof. Accordingly, the composition may include from about 0.1% to about 10% of the indole compound, from about 0.5% to about 5% of the indole compound, or from about 1% to about 2% of the indole compound, for example, wherein the percentage is a weight percentage based on the total weight of the final hair care composition.

Xanthine Compounds

The scalp care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.1% to about 10% of the xanthine compound, from about 0.5% to about 5% of the xanthine compound, or from about 1% to about 2% of the xanthine compound, for example, wherein the percentage is a weight percentage based on the total weight of the final hair care composition. For example, the hair care composition may further include about 0.75% of caffeine.

In an embodiment, the amount of xanthine may be decreased to lessen potential white residue that may result from various formulations when the xanthine is present in higher concentrations. In an embodiment, the hair care composition may comprise from about 0.01% to about 1% xanthine, alternative from about 0.01% to about 0.75% xanthine, alternatively from about 0.01% to about 0.5% xanthine, alternatively from about 0.01% to about 0.25% xanthine, and alternatively from about 0.01% to about 0.1% xanthine. In an embodiment, the hair care composition may have no xanthine.

Vitamin $B_3$ Compounds

The scalp care compositions can further include a vitamin $B_3$ compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. In one embodiment, the composition may include from about 0.1% to about 25% of the vitamin $B_3$ compound; in a further embodiment, from about 0.1% to about 15% of the vitamin $B_3$ compound; in a further embodiment, from about 0.1% to about 7.5%, in another embodiment, from about 3.5% to about 7.5% of the vitamin $B_3$ compound, for example, wherein the percentage is a weight percentage based on the total weight of the final hair care composition. In an embodiment, the scalp care composition may further include about 2.5% of vitamin $B_3$.

Panthenol Compounds

The scalp care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl)]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, in one embodiment, the composition may include from about 0.01% to about 5% of the panthenol compound, in another embodiment, the composition may include from about 0.01% to 2.% of the panthenol compound, in a further embodiment, the composition may include from about 0.05% to about 2% of the panthenol compound; and in another embodiment, the composition may include from about 0.1% to about 1% of the panthenol compound, for example, wherein the percentage is a weight percentage based on the total weight of the final hair care composition. In a further embodiment, the scalp care composition may further include about 0.15% of panthenol.

According to another aspect of the present invention, the scalp care compositions may be free of oleanolic acid and/or biotinyl-GHK, which is contrary to that described in U.S. Patent Application No. 20060067905.

Rheology Modifier

In one embodiment, the scalp care composition comprises a rheology modifier to increase the substantivity of the composition. Any suitable rheology modifier can be used. In an embodiment, the scalp care composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In one embodiment, the scalp care composition may comprise rheology modifiers that are homopolymers based on acrylic acid, methacrylic acid or other related derivatives, non-limiting examples include polyacrylate, polymethacrylate, polyethylacrylate, and polyacrylamide.

In another embodiment, the rheology modifiers may be alkali swellable and hydrophobically-modified alkali swellable acrylic copolymers or methacrylate copolymers non-limiting examples include acrylic acid/acrylonitrogens copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

In a further embodiment, the rheology modifiers may be soluble crosslinked acrylic polymers, a non-limiting example includes carbomers.

In a further embodiment, the rheology modifiers may be alginic acid based materials, non-limiting examples include sodium alginate, and alginic acid propylene glycol esters.

In a further embodiment, the rheology modifier may be an associative polymeric thickeners, non-limiting examples include: hydrophobically modified cellulose derivatives; hydrophobically modified alkoxylated urethane polymers, nonlimiting example include PEG-150/decyl alcohol/SMDI copolymer, PEG-150/stearyl alcohol/SMDI copolymer, polyurethane-39; hydrophobically modified, alkali swellable emulsions, non-limiting examples include hydrophobically modified polypolyacrylates; hydrophobically modified polyacrylic acids, and hydrophobically modified polyacrylamides; hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, in another embodiment from 30-200, in a further embodiment from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

In a further embodiment, the rheology modifier may be cellulose and derivatives, non-limiting examples include microcrystalline cellulose, carboxymethylcelluloses, hydroxyethylcellulose, hydroxypropylcellulose, hydroxypropylmethylcellulose, methylcellulose, ethyl cellulose; nitro cellulose; cellulose sulfate; cellulose powder; hydrophobically modified celluloses.

In an embodiment, the rheology modifier may be a guar and guar derivatives, non-limiting examples include hydroxypropyl guar, and hydroxypropyl guar hydroxypropyl trimonium chloride.

In an embodiment, the rheology modifier may be polyethylene oxide; polypropyne oxide; and POE-PPO copolymers.

In an embodiment, the rheology modifier may be polyvinylpyrrolidone, crosslinked polyvinylpyrrolidone and derivatives. In a further embodiment, the rheology modifier may be polyvinylalcohol and derivatives. In a further embodiment, the rheology modifier may be polyethyleneimine and derivatives.

In another embodiment, the rheology modifier may be silicas, non-limiting examples include fumed silica, precipitated silica, and silicone-surface treated silica.

In an embodiment, the rheology modifier may be water-swellable clays non-limiting examples include laponite, bentolite, montmorilonite, smectite, and hectonite.

In an embodiment, the rheology modifier may be gums non-limiting examples include xanthan gum, guar gum, hydroxypropyl guar gum, Arabia gum, tragacanth, galactan, carob gum, karaya gum, and locust bean gum.

In a further embodiment, the rheology modifier may be, dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of rheology modifiers include acrylamide/ammonium acrylate copolymer (and) polyisobutene (and) polysorbate 20; acrylamide/sodium acryloyldimethyl taurate copolymer/isohexadecane/polysorbate 80, acrylates copolymer, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC); carbomer, crosslinked polyvinylpyrrolidone (PVP), dibenzylidene sorbitol; hydroxyethyl ethylcellulose (EHEC), hydroxypropyl methylcellulose (HPMC), hydroxypropyl methylcellulose (HPMC), hydroxypropylcellulose (HPC); methylcellulose (MC), methylhydroxyethyl cellulose (MEHEC), PEG-150/decyl alcohol/SMDI copolymer, PEG-150/stearyl alcohol/SMDI copolymer, polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, polyurethane-39, sodium acrylate/acryloyldimethyltaurate/dimethylacrylamide, crosspolymer (and) isohexadecane (and) polysorbate 60, sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol Ulterez 30, Carbopol 1342, Sepigel™ 305, Simulgel™600, Sepimax Zen, and combinations thereof.

Carrier

According to another aspect of the present invention, the scalp care compositions may further include at least about 20 weight percent of an aqueous carrier. According to one embodiment, the aqueous carrier may be prepared from demineralized or distilled water, for example. In an embodiment of the present invention, the carrier may comprise water, organic solvents (miscible or non-miscible with water), silicone solvents or a mixture thereof. In one embodiment of the present invention, a volatile carrier may include water or a mixture of water and organic solvents. In a further embodiment, the solvents may be dermatologically acceptable. In one embodiment, the carrier may not comprise more than about 2 wt % of non-volatile solvent. In a further embodiment, the carrier may comprise water with minimal or no significant concentrations of organic solvent, except as otherwise incidentally incorporated into the composition as minor ingredients of other components. In another embodiment, water, organic and silicone solvents that have boiling points below or equal to 250° C. may be volatile solvents and volatile carriers. In one embodiment, solvents with boiling points above 250° C. may be considered non-volatile.

Non-limiting examples of a carrier may include water and water solutions of lower alkyl alcohols and polyhydric alcohol, the lower alkyl alcohols such as monohydric alcohols having 1 to 6 carbons, in one aspect, ethanol and isopropanol, and polyhydric alcohols such as glycols, glycerine and other diols.

Other acceptable carriers that may be used in the aqueous carrier include, but are not limited to alcohol compounds, such as ethanol. According to one embodiment, the composition comprises alcohol, dipropylene glycol, and/or water.

The scalp care compositions may have a pH ranging from about 3.0 to about 10, which may be measured by taking a direct pH measurement using a standard hydrogen electrode of the composition at 25° C. Accordingly, the pH of the hair care composition may be within the range from about 4 to about 9, as a non-limiting example. A non-limiting examples of a pH neutralizer would be tetrahydroxypropyl ethylenediamine, commercially available as Neutrol Te from BASF, triethanolamine (TEA), sodium hydroxide and combinations thereof.

Scalp Benefit Agent

In an embodiment of the present invention, the composition may comprise a scalp benefit agent, a non-limiting example being an anti-dandruff active, which may be a soluble anti-dandruff active. In an embodiment, the anti-dandruff active is selected from the group consisting of: azoles, such as ketoconazole, econazole, climbazole, and elubiol; keratolytic agents such as salicylic acid; and mixtures thereof. In an embodiment, the soluble anti-dandruff active is climbazole.

In an embodiment, the concentration of pyridinethione anti-dandruff particulate ranges from about 0.01% to about 5%, by weight of the composition, or from about 0.1% to about 3%, or from about 0.1% to about 2%. In an embodiment, in addition to the anti-dandruff active selected from soluble actives, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof. In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, isoconazole, sefaconazole, itraconazole, ravuconazole, posaconazole, voriconazole, terconazole, albaconazole, abafungin and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the anti-microbial active is climbazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbazole, octopirox and climbazole, salicylic acid and octopirox, and mixtures thereof. In an embodiment, the concentration of anti-microbials actives ranges from about 0.01% to about 5%, by weight of the composition, or from about 0.1% to about 3%, or from about 0.1% to about 2%.

Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+} A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}(OH)_{3(1-y)}]^+ A^{n-}_{(1-3y)/n} \cdot H_2O$ where the two metal ions ($M^{2+}$) may be the same or different. If they are the same and represented by zinc, the formula simplifies to $[Zn_{1+x}(OH)_2]^{2x+} 2x\ A^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

Polyols

Polyols are a component of the present invention. In an embodiment of the present invention, a nonlimiting example of a polyol is glycerin. Glycerin is a colorless, odorless, viscous liquid that is very common for use in personal care applications and pharmaceutical formulations. Glycerin contains three hydroxyl groups that are responsible for its solubility in water and its humectant nature. Glycerin is well known as hair and skin benefit agent in personal care applications. This material can penetrate into a human hair to provide conditioning and softness via plasticization of the hair fiber while maintaining a very clean surface feel. Glycerin has been observed to clean more hydrophobic soil components (ie. sebum) than water.

The levels of Glycerin range from about 0.1% to about 10%, from about 0.5% to about 8%, from about 1% to about 7% and from about 3.0% to about 6.0% by weight of the shampoo composition.

In another embodiment of the present invention, other polyols may be used. Non-limiting examples include propylene glycol, sugar polyols such as sorbitol, aloe vera gel and honey.

Silicones

The conditioning agent of the compositions of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference. The silicone conditioning agents for use in the compositions of the present invention can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the embodiments of the present invention include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micrometers. The average particle size may be within the range from about 40 nm to about 5 micrometers, from about 50 nm to about 1 micrometers, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

In an embodiment of the present invention, a silicone may be selected from Bis-PEG/PPG-16/16 PEG/PPG 16/16 Dimethicone. A non-limiting example is Abil Care 85 from Evonik.

Organic Conditioning Materials

The conditioning agent of the shampoo compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and it may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Scalp Health Actives

In an embodiment of the present invention, a scalp health active may be added to provide scalp benefits in addition to the anti-fungal/anti-dandruff efficacy provided by the ZPT. This group of materials is varied and provides a wide range of benefits including moisturization, barrier improvement, anti-fungal, and anti-oxidant, anti-itch, and sensates. Such skin health actives include but are not limited to: vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, iso cyclomone, benzyl alcohol, and natural extracts/oils including peppermint, spearmint, argan, jojoba and aloe.

Optional Ingredients

The compositions of the present invention can also additionally comprise any suitable optional ingredients as desired. For example, the composition can optionally include other active or inactive ingredients.

The compositions may include other common hair ingredients such as pyrithione zinc, minoxidil, silicones, glycerin, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, rinse-off hair products such as conditioners, shampoos, and treatment products; and any other form that may be applied to the hair and preferably applied to the scalp.

II. Methods

Zone of Inhibition

The Zone of Inhibition (ZOI) methodology is used for this evaluation. In the ZOI method, *Malassezia* yeast organisms are seeded on a petri dish filled with growth medium. In this experiment, 100 µl of diluted (1:500 in vehicle) leave-on treatment is placed in wells on agar plates, which are then incubated. The applied product diffuses radially over time, with the anti-fungal potency indicated by the inhibition of fungal growth circularly from the center. The diameter of this circular inhibition is measured, the larger the circle, the more potent the anti-fungal activity of the product. Each leg has 10 plates and each plate 2 measurements. The zone is measured both along the length and width. Averages are plotted along with standard deviation. Student t test is used to group formulas at a significance level of 0.1.

In FIG. 1, the composition A (included as Example 1) is demonstrated to have improved anti-fungal activity over that of composition B (composition of Example 1 without Butylene Glycol and Benzyl Alcohol solvents). Composition A demonstrates a 10.5% increase in anti-fungal activity and efficacy.

It can be visually noted that the turbidity of composition B is higher than that of composition A, which, without being bound by theory, is thought to be the result of reduced climbazole solubility. As solubility of the active, climbazole, increases the % Transmission of visible light through a sample, is observed as a decrease in opacity.

In an embodiment of the present invention, the anti-dandruff active is one which is readily soluble in carriers and/or matrix and forms a substantially clear (% Transmittance.gtoreq.80 at 600 nm) solution in carriers and/or matrix. The transparency of the composition may be measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Formulations and Examples

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

TABLE 1

| Examples | | |
|---|---|---|
| | Examples 1 Active wt %) | Comparative Examples 2 Active wt % |
| Water | Q.S. | Q.S. |
| Alcohol 100% (Ethanol) | 50 | 50 |
| Acrylates/C10-30 alkyl acrylate crosspolymer *1 | 0.35 | 0.35 |
| Bis-PEG/PPG-16/16 PEG/PPG 16/16 Dimethicone *2 | 0.7 | 0.7 |
| Panthenol *3 | 0.15 | 0.15 |
| Niacinamide *4 | 2.5 | 2.5 |
| Caffeine *5 | 0.75 | 0.75 |
| Climbazole *6 | 0.50 | 0.50 |
| Butylene Glycol *7 | 1.0 | 0 |
| Benzyl Alcohol *8 | 0.5 | 0 |
| Tetrahydroxypropyl Ethylenediamine *9 | 0.05 | 0.05 |

*1 as in Carbopol Ultrez 21 available from Lubrizol
*2 as in Abil Care 85 from Evonik
*3 as in Dexapaanthenol USP from Roche vitamins
*4 as in Niancinamide USP from Roche Vitamins
*5 as in Caffeine USP from BASF
*6 as in Crinipan AD from Symrise
*7 as in Cosmetic Quality 1,3-Butylene Glycol from Oxea Corporation
*8 as in Benzyl Alcohol from Polarome International
*9 as in Neutrol Te from BASF Examples 1 is representative of the present invention. Example 2 is a comparative example. Example 2 does not deliver the desired benefit that the present invention delivers because it is believed that it does not contain the efficacious solvents.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A scalp care composition comprising:
   a) from about 0.05% to about 5% of an anti-dandruff active;
   b) from about 0.1% to about 25% of one or more organic solvents wherein the organic solvent is selected from butylene glycol, benzyl alcohol and mixtures thereof;
   c) from about 1% to about 99% of a volatile carrier; and
   wherein the anti-dandruff active is soluble in the scalp care composition.

2. The scalp care composition according to claim 1 wherein at least about 0.1 g of the anti-dandruff active dissolves in 100 ml of the organic solvent, at 25° C. and 1 atm of pressure.

3. The scalp care composition according to claim 1 wherein the scalp care composition results in a 10.5% increase in efficacy in a zone of inhibition vs. a composition without butylene glycol or benzyl alcohol solvents.

4. The scalp care composition according to claim 1 wherein there is an increase in % transmission of visible light as compared to a composition which does not comprise the same organic solvent(s) or volatile carriers.

5. The scalp care composition according to claim 1 wherein the soluble anti-dandruff active is an azole.

6. The scalp care composition according to claim 5 wherein the azole is selected from imidazoles, thiazoles, triazoles and mixtures thereof.

7. A scalp care composition according to claim 6 wherein the imidazole is selected from climbazole, benzimidazole, benzothiazole, bifonazole, butaconazole nitrate, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, isoconazole, sefaconazole, itraconazole, ravuconazole, posaconazole, voriconazole, terconazole, albaconazole, abafungin, terconazole, itraconazole and mixtures thereof.

8. The scalp care composition according to claim 7 wherein the imidazole is climbazole.

9. The scalp care composition according to claim 1 wherein the organic solvent is from about 1.0% to about 15%.

10. The scalp care composition according to claim 1 wherein the soluble anti-dandruff active is from about 0.3% to about 2%.

11. The scalp care composition according to claim 1 wherein the volatile carrier is water or a mixture of water and organic solvents.

12. The scalp care composition according to claim 1 further comprising from about 0.05% to about 10% of a polymeric rheology modifier.

13. The scalp care composition according to claim 12 wherein the polymeric rheology modifier is selected from the group consisting of is selected from the group consisting of hydrophobically modified hydroxyethyl celluloses, hydrophobically modified polypolyacrylates, hydrophobically modified polyacrylic acids, hydrophobically modified polyacrylamides, and hydrophobically modified polyethers and mixtures thereof.

14. The scalp care composition according to claim 1 wherein the composition further comprises niacinamide in the range of 0.1% to 7.5%.

15. The scalp care composition according to claim 1 wherein the composition further comprises caffeine in the range of 0.1% to 3.0%.

16. The scalp care composition according to claim 1 wherein the composition further comprises panthenol in the range of 0.01% to 2.0%.

17. The scalp care composition according to claim 1 wherein the composition further comprises a silicone.

18. The scalp care composition according to claim 1 wherein the composition is a leave-on composition.

* * * * *